(12) United States Patent
Takeo

(10) Patent No.: US 6,381,348 B2
(45) Date of Patent: *Apr. 30, 2002

(54) NETWORK SYSTEM FOR MEDICAL IMAGES

(75) Inventor: Hideya Takeo, Kanagawa-ken (JP)

(73) Assignee: Fuji Photo Film Co., Ltd., Kanagawa (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/141,520

(22) Filed: Aug. 27, 1998

(30) Foreign Application Priority Data

Aug. 29, 1997 (JP) .............................. 9-234398

(51) Int. Cl.⁷ ................................................ G06K 9/00
(52) U.S. Cl. ...................................... 382/128; 128/922
(58) Field of Search ................................ 382/128, 129, 382/130, 132, 131; 700/102; 600/509; 358/500; 710/7; 359/143

(56) References Cited

U.S. PATENT DOCUMENTS

| | | | | |
|---|---|---|---|---|
| 4,739,521 A | * | 4/1988 | Akimoto | 455/612 |
| 4,951,201 A | * | 8/1990 | Takeo et al. | 382/413.13 |
| 5,111,285 A | * | 5/1992 | Fujita et al. | 358/75 |
| 5,412,774 A | * | 5/1995 | Agrawal et al. | 395/157 |
| 5,539,914 A | * | 7/1996 | Fry et al. | 395/827 |
| 5,619,708 A | * | 4/1997 | Ho | 395/767 |
| 5,735,285 A | * | 4/1998 | Albert et al. | 128/696 |
| 5,881,170 A | * | 3/1999 | Takeo et al. | 382/199 |
| 5,930,799 A | * | 7/1999 | Tamano et al. | 700/102 |

* cited by examiner

*Primary Examiner*—Joseph Mancuso
*Assistant Examiner*—Abolfazl Tabatabai
(74) *Attorney, Agent, or Firm*—Sughrue Mion, PLLC

(57) ABSTRACT

Appropriate image processing is carried out on image information input to a network. Processing completion or incompletion judging means in a QC-WS reads header information of image information input from an image information inputting apparatus to the network, and judges whether or not the image information has been processed. If the image information has been judged as processing incomplete, the information is sent to an image processing apparatus to be processed thereby and output from an image information outputting apparatus. If the image information has been judged as processing complete, the image information is output from the image information outputting apparatus as it is.

15 Claims, 4 Drawing Sheets

NETWORK SYSTEM FOR MEDICAL IMAGES

BACKGROUND OF THE INVENTION

1. Field of the Invention

The present invention relates to an image processing system, and more specifically, to a medical image network system to which image information which has already been processed and information which has not been processed is input coexistently.

2. Description of the Related Art

In the field of medicine, various kinds of diagnostic image generating apparatuses (modalities) using X rays or the like have been in use and Computed Radiography (CR) apparatuses, Computed Tomography (CT) apparatuses, Magnetic Resonance Imaging (MRI) apparatuses, and the like have been put into practice. An image generated by each modality is displayed on a CRT or output on a film by a Laser Printer (LP) or the like, and used at a medical facility for diagnosing a lesion or an injury, and the degree thereof.

A CR (computed radiography) apparatus is a radiation image reading recording system which obtains an image signal by using stimulable phosphor which emits light upon exposure to stimulating rays such as visible light or a laser beam in accordance with the radiation energy which has been stored in the material. Radiation image information based on a human body or the like is temporarily recorded on a stimulable phosphor sheet, and the stimulable phosphor sheet is scanned by a stimulating ray such as a laser beam to cause it to emit light, and the light emitted is photoelectrically read to obtain an electric signal. Recently, the CR apparatuses have-been in wide use and put into practice. As an aspect of a CR apparatus to be connected to a network system which will be explained later, not only the above described entire radiation image reading recording system but also a single radiation image information reading apparatus which can input a read out image signal (image information) to the network may be used, for example.

Following recent improvement in communications and computer technologies, a variety of networks using computers are being installed in hospitals. Each modality in the above, which has been used in a stand alone mode, is becoming a portion of the network as an image information inputting apparatus, and so are CRT displays and LPs as image outputting apparatuses.

Meanwhile, these image information inputting apparatuses (image generating apparatuses) and image outputting apparatuses have been manufactured on a premise that they will be used in a stand alone mode. Therefore, there has been no compatibility in formats of image information when image information is input or output between these apparatuses. However, following the recent development of networking technology, this problem is being solved.

Nevertheless, the image information inputting apparatuses are originated in systems which used to carry out output of individual visible images, as has been described above. Therefore, image information input from an image information inputting apparatus to a network may have been image-processed by the image information inputting apparatus. It is common practice for modalities other than CR apparatuses to output image information which has already been processed, and image information input to a network is generally assumed to be image information having been processed (processing complete). However, image information input from a CR apparatus is not necessarily the information of an image which has been processed (processing incomplete), and the image information input from an apparatus other than CR apparatuses is not always the image information which has already been processed, either.

As has been described above, it is possible for image information which has been processed and information that has not been processed to coexist on a network. When image information input in such a manner is output to various kinds of image information outputting apparatuses, image processing appropriate for the apparatuses may be necessary.

However, for image information which has already been processed by an image information inputting apparatus, it may not be appropriate in some cases to further carry out uniform image processing on the network.

SUMMARY OF THE INVENTION

The present invention has been created based on consideration of the above problems, and its object is to provide a medical image network system which enables appropriate image processing on the network, even when image information having been processed and image information not having been processed is input coexistently from image information inputting apparatuses.

In a first medical image network system of the present invention, image information input to the network has process completion or incompletion information as header information thereof showing whether or not image processing has been carried out thereon, and the network either causes an image processing apparatus to carry out image processing on the image information or causes an image information outputting apparatus to output the image information without processing thereby, based on this information.

In other words, the first medical image network system of the present invention connects an image information inputting apparatus such as a CR apparatus, a CT apparatus, and an MRI apparatus for inputting image information representing a medical image, and an image information outputting apparatus such as a CRT and an LP for reproducing the image information as a visible image, has:

processing completion or incompletion information as header information or the like of image information input to the network showing whether or not predetermined image processing (such as frequency enhancing (or smoothing) processing, tone processing, enlargement or reduction processing, or the like) has been carried out on the image information; and comprises processing completion or incompletion judging means which reads the processing completion or incompletion information from the image information having been input to the network and judges whether or not the image information has been image-processed; and an image processing apparatus which carries out predetermined image processing such as frequency enhancing (or smoothing) processing, tone processing, or enlargement or reduction processing on image information which has been judged by the processing completion or incompletion judging means as image processing incomplete.

Image information which has been judged as processing complete by the processing completion or incompletion judging means may be output as it is from the network to an image information outputting apparatus, or may be output after general processing thereon to fit the information to a format of the image information outputting apparatus.

As a method of image processing by the image processing apparatus, the image processing apparatus may have a default image processing condition so that image processing is carried out on image information which has not been processed according to the condition, or image processing may be carried out after a processing condition is decided based on the header information of the input image information or attached information other than that. Alternatively, an image processing condition and the content of the processing may be transferred from the image information inputting apparatus to the image processing apparatus so that the image processing is carried out based thereon.

In a second medical image network system of the present invention, the image information input to the network has image processing completion or incompletion information as header information or the like of the image information showing whether or not the image information has been processed so that an image processing apparatus can carry out image processing on the image information based thereon, and image quality judgment is carried out on image information which has been processed by the image processing apparatus or image information input after image processing has been carried out thereon by an image information inputting apparatus, in order to output the image information to an image information outputting apparatus after image processing is again carried out thereon as required.

In other words, the second medical image network system of the present invention connects an image information inputting apparatus for inputting image information representing a medical image, and an image information outputting apparatus for reproducing the image information as a visible image, has processing completion or incompletion information as header information or the like of the image information input to the network showing whether or not predetermined image processing (such as frequency enhancing (or smoothing) processing, tone processing, enlargement or reduction processing, or the like) has been carried out on the image information; and comprises:

processing completion or incompletion judging means which reads the processing completion or incompletion information from the image information having been input to the network and judges whether or not the image information has been image-processed;

an image processing apparatus which carries out predetermined image processing on image information which has been judged by the processing completion or incompletion judging means as image processing incomplete; and image quality judging means which comprises a monitor unit such as a display apparatus for inputting image information having been judged as processing complete by the processing completion or incompletion judging means and image information having been processed by the image processing apparatus and for reproducing a visible image representing the image information, a judgment inputting unit for receiving input of judgment regarding image quality of the visible image, and an outputting unit for outputting image information whose quality judgment result is fair to the image information outputting apparatus and for returning image information whose quality judgment result is not fair to the image information inputting apparatus.

The judgment inputting unit may function as an input unit comprising inputting means whereby an operator or the like observing a visible image reproduced by the monitor unit directly inputs a judgment result to the image quality judging means, or may function as an input unit which receives a judgment result from the image information inputting apparatus input by the operator or the like, when the monitor unit of the image quality judging means is installed near the image information inputting apparatus (in this case, the input unit does not need inputting means of its own).

Image information which has been returned to the image information inputting means by the image quality judging means is re-processed according to the same processing condition, or according to a processing condition having been changed from the previous one, to be input again to the image quality judging means. The operator or the like inputs whether or not the processing condition is changed, a new processing condition if changed, and a judgment result, to the judgment inputting unit. Alternatively, the operator or the like may input a processing condition by choosing an appropriate one from a plurality of pre-set processing conditions.

According to the first medical image network system of the present invention, image information to be input to the network has processing completion or incompletion information as header information or the like of the image information showing whether or not image processing has been carried out thereon, and the processing completion or incompletion judging means sends the image information to the image processing apparatus or to the image information outputting apparatus as it is, based on this information. The image information sent to the image processing apparatus has not been processed, and by outputting the image information on which the image processing apparatus has carried out image processing to the image information outputting apparatus, the image information can be output properly to the image information outputting apparatus after appropriate image processing carried out thereon on the network, even in the case where image information having been image-processed and image information not having been processed is input coexistently from the image information inputting apparatus.

According to the second medical image network system of the present invention, image information to be input to the network has processing completion or incompletion information as header information or the like of the image information showing whether or not image processing has been carried out thereon, and the processing completion or incompletion judging means sends the image information to the image processing apparatus or to the image quality judging means as it is, based on this information. The image information sent to the image processing apparatus has not been processed, and the image information is output to the image quality judging means after the image processing apparatus has carried out image processing thereon. The image information having been processed (including both the information processed by the image processing apparatus and the information which had been processed before it was input from the image information inputting apparatus) and input to the image quality judging means is reproduced by the monitor unit. Based on a judgment result input from the image quality judging means, the image information is returned to the image processing apparatus to be re-processed thereby, or output to the image information outputting apparatus. In this manner, even in the case where image information having been image-processed and image information not having been processed is input coexistently from the image information inputting apparatus, the image information can be output properly to the image information outputting apparatus after appropriate image processing has been carried out thereon on the network.

DESCRIPTION OF THE PREFERRED EMBODIMENTS

Hereinafter, embodiments of medical image network systems of the present invention will be explained with reference to the accompanying drawings.

Figure 1:
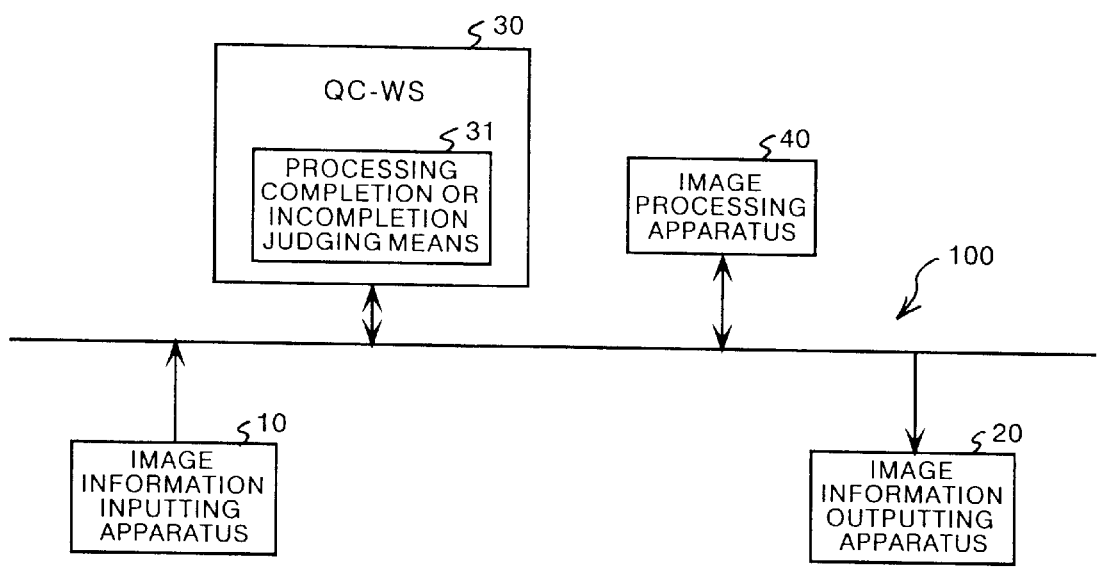
FIG. 1 is a schematic diagram showing a first embodiment of a medical image network system of the present invention.

FIG. 1 is a schematic diagram showing a first medical image network system 100 of the present invention.

The network system 100 in FIG. 1 is a medical image network system to which image information inputting apparatuses 10 including plural kinds of image inputting modalities (such as a CR apparatus, a CT apparatus, an MRI apparatus, an RI apparatus, and other image inputting modalities), and image information outputting apparatuses 20 including plural kinds of image outputting apparatuses (such as a CRT display, an LP, and other image outputting apparatuses) are connected. Image information input to this network 100 has processing completion or incompletion information as header information thereof showing whether or not predetermined image processing has been carried out on the input image information. The medical image network system further comprises processing completion or incompletion judging means 31 which reads this processing completion or incompletion information from the header information of the image information input to this network and judges whether or not the image information has been processed, and an image processing apparatus 40 which carries out predetermined image processing on image information having been judged as processing incomplete by the processing completion or incompletion judging means 31.

The processing completion or incompletion judging means 31 is an element composing an image quality control (quality assurance) work station 30, which is called a QC Work Station (QC-WS) on the network 100 and totally controls or assures image information quality (image quality). In this embodiment, explanation regarding the QC-WS 30 (in the case of an image quality assurance work station, it is called a QA-WS) is omitted here.

Image information input from each image information inputting apparatus 10 to the network 100 will be explained next.

As has been explained above, the network 100 connects various kinds of image inputting modalities such as a CR apparatus, a CT apparatus, and an MRI apparatus as the image information inputting apparatus 10. Image information input from the CR apparatus shows information of an image wherein an emitted radiation has been converted according to a predetermined conversion characteristic. Therefore, although the image information depends on the conversion characteristic of the CR apparatus, image processing has not been carried out thereon. On the other hand, image information input from the image information inputting apparatuses 10 other than the CR apparatus, such as the CT apparatus or the MRI apparatus, has been image-processed by the image information inputting apparatus 10.

Figure 2:
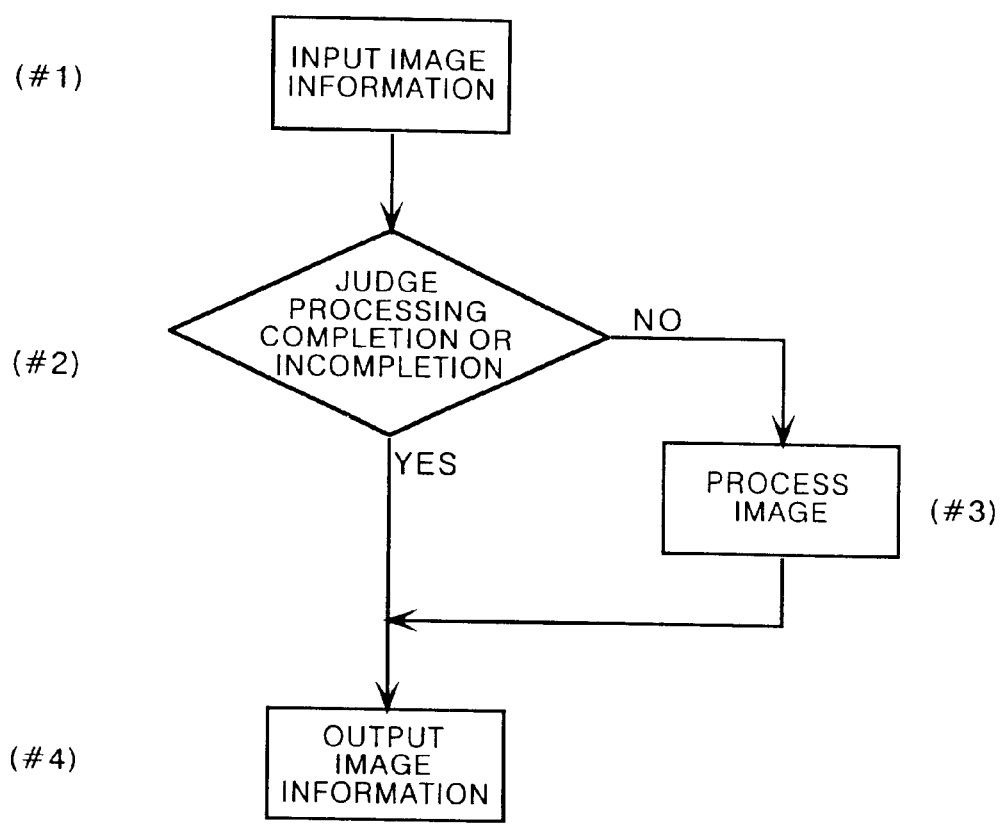
FIG. 2 is a diagram showing an algorithm of an operation of the network system shown in FIG. 1.

An operation of the network system 100 of the present embodiment will be explained with reference to FIGS. 1 and 2. FIG. 2 is an algorithm showing the operation of the network system 100 in this embodiment.

Image information input from any one of the image information inputting apparatuses 10 to the network is input to the processing completion or incompletion judging means 31 in the QC-WS 30 (Step #1 in FIG. 2). The processing completion or incompletion judging means 31 reads the header information of the input image information and judges whether or not the image information has been image-processed (Step #2 in FIG. 2).

Image information which has been judged as processing incomplete is sent to the image processing apparatus 40 (Step #2) to be processed thereby (Step #3) and output to the image outputting apparatus 20.

Meanwhile, image information which has been judged as processing complete by the processing completion or incompletion judging means 31 is sent to the image information outputting apparatus 20 as it is (Step #2).

The image information outputting apparatus 20 outputs the image information input from the image processing apparatus 40 or processing completion or incompletion judging means 31 as a visible image.

As has been described above, according to the medical image network system of the present invention, image information can be output to the image information outputting apparatus after appropriate image processing has been carried out thereon on the network, even when image information which has been image-processed and image information which has not been processed is input coexistently from the image information inputting apparatuses to the network.

Figure 3:
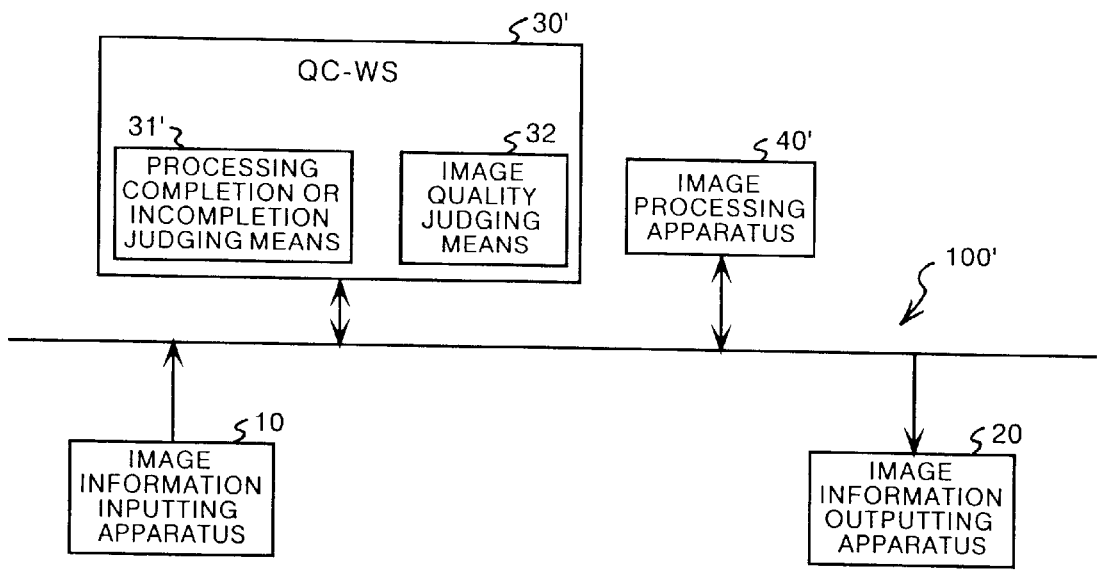
FIG. 3 is a schematic diagram showing a second embodiment of a medical image network system of the present invention.

FIG. 3 is a diagram showing an outline of a second medical image network system 100' of the present invention.

The network system 100' in FIG. 3, like the network system 100 in FIG. 1, is a medical image network system to which image information inputting apparatuses 10 including plural kinds of image inputting modalities and image information outputting apparatuses 20 including plural kinds of image outputting devices are connected. Image information input to this network 100' has processing completion or incompletion information as header information of the image information showing whether or not predetermined image processing has been carried out on the input image information. The medical image network system 100' further comprises processing completion or incompletion judging means 31' which reads this processing completion or incompletion information from the header information of the image information input to this network and judges whether or not the image information has been processed, an image processing apparatus 40' which carries out predetermined image processing on image information having been judged as processing incomplete by the processing completion or incompletion judging means 31', image quality judging means 32 comprising a monitor unit such as a display apparatus for inputting image information having been judged as processing complete by the processing completion or incompletion judging means and image information having been processed by the image processing apparatus 40' and for reproducing a visible image representing the image information, a judgment inputting unit for receiving input of judgment regarding image quality of the visible image, and an outputting unit for outputting image information whose quality judgment result is fair to the image information outputting apparatus 20 and for outputting image information whose quality judgment result is not fair to the image information processing apparatus 40'.

The processing completion or incompletion judging means 31' and image quality judging means 32 are the elements composing an image quality control (quality assurance) work station 30' on the network 100.

The judgment inputting unit has a function whereby an operator or the like observing the visible image reproduced by the monitor unit can input a judgment result.

Image information returned to the image processing apparatus 40' by the image quality judging means 32 is processed according to the same processing condition or according to a different condition, and input again to the image quality judging means 32. At this time, the operator or the like can input to the judgment inputting unit whether or not the processing condition is changed and the new processing condition if it is changed, as well as the judgment result.

Figure 4:
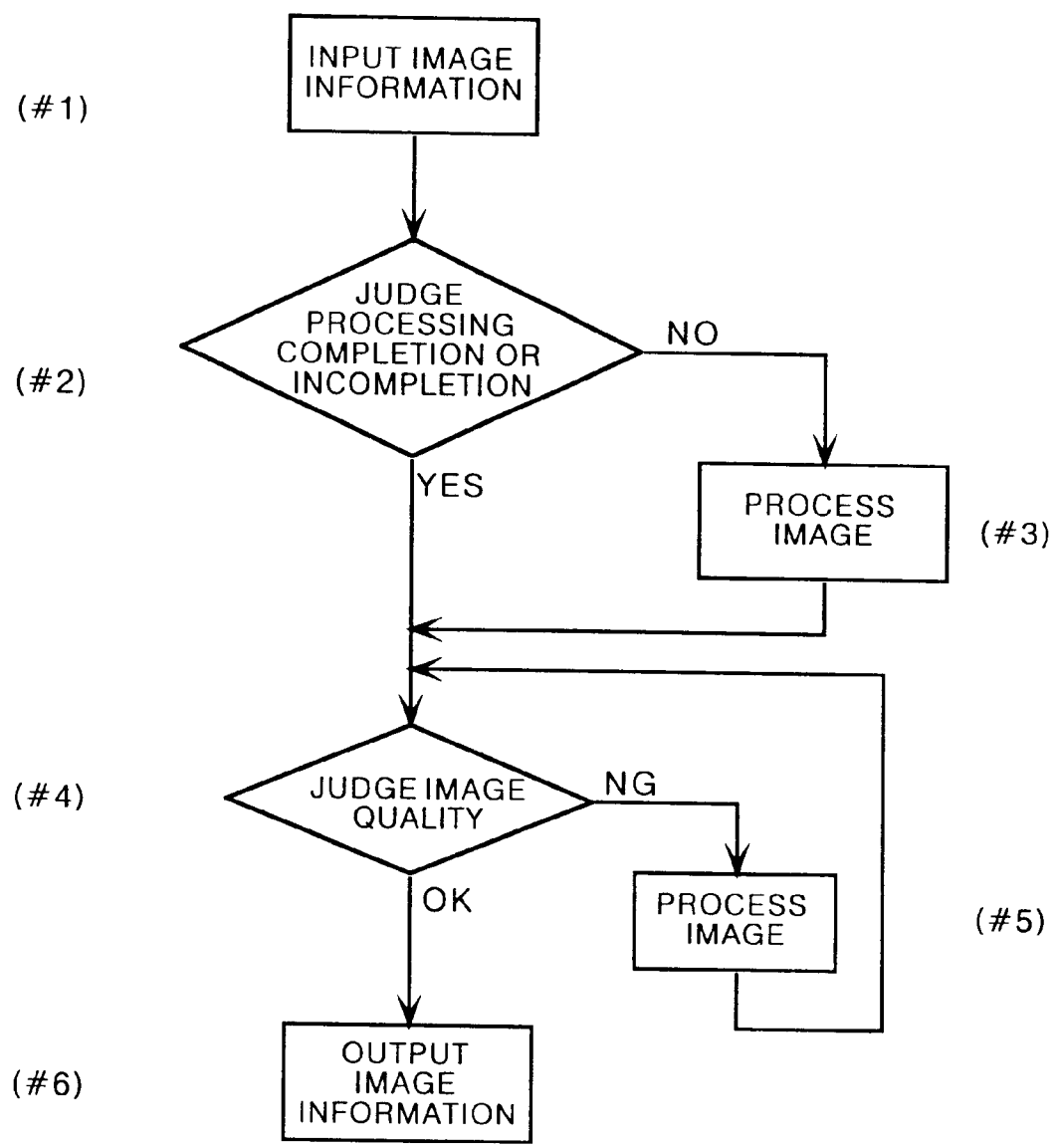
FIG. 4 is a diagram showing an algorithm of an operation of the network system shown in FIG. 3.

An operation of the network system 100' of this embodiment will be explained with reference to FIGS. 3 and 4. FIG. 4 is an algorithm showing the operation of the network system 100'.

Image information input from any one of the image information inputting apparatuses 10 to the network 100' is first input to the processing completion or incompletion judging means 31' in the QC-WS 30' (Step #1 in FIG. 4). The processing completion or incompletion judging means 31' reads the header information of the input image information and judges whether or not the image information has been image-processed (Step 2 in FIG. 4).

The image information judged as processing incomplete by the processing completion or incompletion judging means is sent to the image processing apparatus 40' (Step #2) to be processed thereby (Step #3), and output to the image quality judging means 32.

Meanwhile, the image information judged as processing complete by the processing completion or incompletion judging means 31' is sent to the image quality judging means 32 as it is (Step #2).

The monitor unit of the image quality judging means 32 reproduces a visible image represented by the input image information having been image-processed, and the operator confirms this reproduced image. The operator judges whether the image can be output from the image information outputting apparatus 20 as it is or if it needs further image processing, and inputs the judgment result to the judgment inputting means (Step #4). At this time, if the judgment result showing that it needs more image processing is input, a processing condition for the additional image processing is also input to the judgment inputting means.

The image quality judging means 32 returns the image information to the image processing apparatus 40' (Step #4) together with the additional processing condition having been input to the judgment result inputting unit, if the judgment result input to the judgment result inputting unit shows the necessity of additional image processing.

The image processing apparatus 40' carries out image processing on the image information having been input from the image quality judging means 32 according to the processing condition which has also been input from the image quality judging means 32 (Step #5), and outputs the image information to the image quality judging means 32. The image quality judging means 32 repeats the image processing and the judgment processing (Steps #5 to #4) until the judgment result on the reproduced image displayed on the monitor unit shows that it may be output from the image information outputting apparatus 20.

If the image information whose judgment result input to the judgment inputting unit of the image quality judging means 32 shows that it mat be output from the image information outputting apparatus 20, the image information is output to the image information outputting apparatus 20 (Step #4).

The image information outputting apparatus 20 outputs the image information input from the image quality judging means 32 as a visible image.

As has been described above, according to the medical image network system of the present invention, image information can be output to the image information outputting apparatus after appropriate image processing has been carried out thereon on the network, even when image information which has been image-processed and image information that has not been processed is input coexistently from the image information inputting apparatuses to the network.

What is claimed is:

1. A medical image network system having an image information inputting apparatus for inputting image information representing a medical image connected with an image information outputting apparatus for reproducing the image information as a visible image, said image inputting apparatus providing the medical image of an object being imaged by exposing the object to an electromagnetic source, said system comprising:

a processing completion or incompletion judging means for reading processing completion or incompletion information from at least one of: a header portion and data portion of the image information having been input to the network and judging whether or not the image information has been image-processed based on the processing completion or incompletion information; and an image processing apparatus for carrying out predetermined image processing on image information that has been judged by the processing completion or incompletion judging means as image processing incomplete.

2. A medical image network system having an image information inputting apparatus for inputting image information representing a medical image connected with an image information outputting apparatus for reproducing the image information as a visible image, said system comprising:

a processing completion or incompletion judging means for reading processing completion or incompletion information from at least one of: a header portion and data portion of the image information having been input to the network and judging whether or not the image information has been image-processed based on the processing completion or incompletion information;

an image processing apparatus for carrying out predetermined image processing on image information that has been judged by the processing completion or incompletion judging means as image processing incomplete; and image quality judging means comprising a monitor unit for inputting information having been judged as processing complete by the processing completion or incompletion judging means and image information having been processed by the image processing apparatus and for reproducing a visible image representing the image information, a judgment inputting unit for receiving input of judgment regarding image quality of the visible image, and an outputting unit for outputting image information whose quality judgment result is fair to the image information outputting apparatus and for returning image information whose quality judgment result is not fair to the image processing apparatus for additional processing.

3. The medical image network system according to claim 1, wherein said header information indicates whether the image information has been subject to at least one of frequency enhancement, tone processing, enlargement processing, and reduction processing.

4. The medical image network system according to claim 2, wherein said header information indicates whether the image information has been subject to at least one of frequency enhancement, tone processing, enlargement processing, and reduction processing.

5. A medical image network comprising:

a plurality of imaging apparatuses for inputting image information representing a medical image, which each output image information including a header portion to indicate whether the image information has undergone refinement image processing;

a header reader for reading the header portion; and an image refinement apparatus for further processing the image information based on a state of the header portion.

6. The image network according to claim 5 further comprising:

a monitor to output a visible image processed by the image refinement apparatus; and an input device operable by a user to transmit the image information to the image refinement apparatus when the visible image has an unacceptable quality.

7. The image network according to claim 6 further comprising a reproduction device to reproduce the visible image displayed on the monitor when the visible image is determined to have acceptable quality.

8. The medical image network system according to claim 1, wherein said at least one of said header portion and said data portion indicates whether the image information has been subject to at least one of frequency enhancement, tone processing, enlargement processing, and reduction processing.

9. The medical image network system according to claim 2, wherein said at least one of said header portion and said data portion indicates whether the image information has been subject to at least one of frequency enhancement, tone processing, enlargement processing, and reduction processing.

10. The medical image network system according to claim 3, wherein said network transmits image information which has undergone predetermined image processing and further transmits image information which has not undergone predetermined processing.

11. The medical image network system according to claim 4, wherein said network transmits image information which has undergone predetermined image processing and further transmits image information which has not undergone predetermined processing.

12. The image network according to claim 5, wherein said network transmits image information which has undergone refinement image processing and further transmits image information which has not undergone refinement image processing.

13. The system of claim 1, wherein said image inputting apparatus provides the medical image from a multi-dimensional spatial scan of the object being imaged.

14. The system of claim 13, wherein said medical image is formed from at least one of: a CT process, a CR process, and an MRI process.

15. The system of claim 1, wherein said image inputting apparatus detects irradiation emitted by the object as a result of exposing the object to the electromagnetic source.

* * * * *